(12) United States Patent
Schubert et al.

(10) Patent No.: US 7,214,808 B2
(45) Date of Patent: May 8, 2007

(54) METHOD FOR THE PRODUCTION OF 4-(17α-SUBSTITUTED-3-OXOESTRA-4,9-DIEN-11β-YL)BENZALDEHYDE-(1E)-OXIMES

(75) Inventors: Gerd Schubert, Jena (DE); Sven Ring, Jena (DE); Bernd Erhart, Kahla (DE)

(73) Assignee: Schering AG, Berlin (DE)

( * ) Notice: Subject to any disclaimer, the term of this patent is extended or adjusted under 35 U.S.C. 154(b) by 578 days.

(21) Appl. No.: 10/416,029

(22) PCT Filed: Nov. 9, 2001

(86) PCT No.: PCT/DE01/04218

§ 371 (c)(1),
(2), (4) Date: Oct. 15, 2003

(87) PCT Pub. No.: WO02/38582

PCT Pub. Date: May 16, 2002

(65) Prior Publication Data

US 2004/0053905 A1 Mar. 18, 2004

(30) Foreign Application Priority Data

Nov. 10, 2000 (DE) .............................. 100 56 676

(51) Int. Cl.
*C07J 1/00* (2006.01)
(52) U.S. Cl. .................................... 552/648
(58) Field of Classification Search ................ 552/648
See application file for complete search history.

(56) References Cited

U.S. PATENT DOCUMENTS 5,576,310 A 11/1996 Schubert et al.
5,693,628 A * 12/1997 Schubert et al. ............ 514/179

FOREIGN PATENT DOCUMENTS

EP 0648778 4/1995

OTHER PUBLICATIONS

Sova et al., "Modification of steroids in the androstane series with three-membered heterocycles at C(17)." Khimiko-Farmatsevticheskii Zhurnal, vol. 23(9), pp. 1088-1091, 1989, English Abstract only.*

Journal of the American Chemical Society; vol. 84, Oct. 5, 1962 No. 19, pp. 3782-3783.

C. Rücker et al., "Funktionalisierte Dioxide (syn-1,3) und Trioxide (syn, syn; syn, anti) des Tropilidens," Chemische Berichte., 1984, pp. 1801-1833, vol. 117, No. 5, XP002197491, Verlag Chemie GmbH, Weinheim, DE, ISSN: 0009-2940; p. 1816, example 37,50; p. 1830, abstract 5. English Abstract Only.

W. Seppelt et al., "Funktionalisierte Dioxide (syn-1,4) und Trioxide (anti, anti) des Tropilidens," Chemische Berichte, 1984, pp. 1834-1855, vol. 117, No. 5, XP002197492, Verlag Chemie GmbH, Weinheim, DE, ISSN: 0009-2940; p. 1837, example 11,13; p. 1838, example 3,15. English Abstract Only.

Kuwahara S et al., "Synthesis of Levo Periplanone-B a Sex Phormone Component of the American Cockroach Periplaneta-Americana," Tetrahedron, 1990, pp. 8075-8082, vol. 46, No. 24, ISSN: 0040-4020, p. 8078, figure 4.

T. K. Dhar et al., "Structure of phaseolinone, a novel phytotoxin from macrophomia phaseolina," Tetrahedron Letters, 1982, pp. 5459-5462, vol. 23, No. 51, XP002197494, Elsevier Science Publishers, Amesterdam, NL, ISSN: 0040-4039, p. 5459, abstract 3; p. 5460, example 1, 7.

* cited by examiner

*Primary Examiner*—Barbara P. Badio
(74) *Attorney, Agent, or Firm*—Millen, White, Zelano & Branigan, P.C.

(57) ABSTRACT

The invention relates to a method for the production of 4-(17α substituted 3-oxoestra-4,9-dien-11β-yl)benzaldehyd-(1E or 1Z)-oximes of general formula (I), where $R_1$=H, $C_{1-6}$ alkyl or a $C_nF_{2n+1}$ group; $R_2$=$C_{1-4}$ alkyl, X=E- or Z-OH; and Y=O—$C_{1-6}$ alkyl, S—$C_{1-6}$ alkyl or O—$CH_2C_nF_{2n+1}$, where n=1, 2 or 3, which produces the target compounds of formula (I) with high yield and selectivity.

9 Claims, No Drawings

METHOD FOR THE PRODUCTION OF 4-(17α-SUBSTITUTED-3-OXOESTRA-4,9-DIEN-11β-YL)BENZALDEHYDE-(1E)-OXIMES

This application is a §371 of PCT/DE01/04218, filed Nov. 9, 2001.

A process for the production of 4-(17α-substituted-3-oxoestra-4,9-dien-11β-yl)benzaldehyde-(1E or 1Z)-oximes of general formula (I) is provided

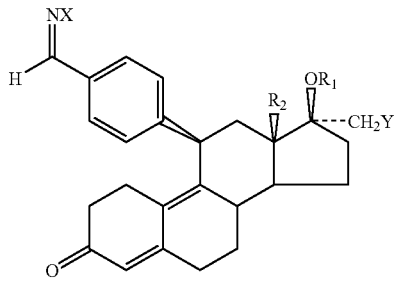

(I)

in which $R_1$ means a hydrogen atom, a $C_{1-6}$-alkyl radical or a $C_nF_{2n+1}$ radical, $R_2$ means a $C_{1-4}$-alkyl radical, X means an OH group in E- or Z-position, and Y means an $OC_{1-6}$-alkyl group, an $SC_{1-6}$-alkyl group or an $OCH_2C_nF_{2n+1}$ group, whereby n is 1, 2 or 3.

4-(17α-Substituted-3-oxoestra-4,9-dien-11β-yl)benzaldehyde-(1E or 1Z)-oximes are already known. Substances of this type are described in Patent DE 4332283 A1 (EP 0 648 778 B1). Because of the advantageous antigestagenic action and a slight antiglucocorticoidal action, the compounds are of general interest for treating a number of hormone-dependent female diseases, such as, for example, endometriosis.

The existing process for their production preferably uses as a starting material 5α,10α-epoxy-estr-9(11)-en-17-one (IIa) that is protected as a dimethyl ketal on a C-3 as a ketal,

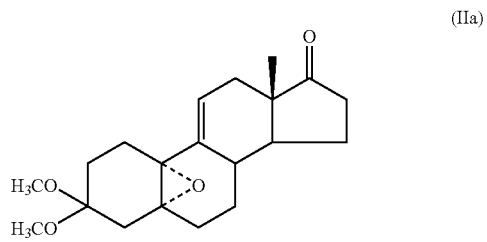

(IIa)

and thus allows the production of both selectively a number of various 11β-aryl-substituted steroids and different 17α-substituted compounds. In a first step, the 5α,10α-epoxide of formula (IIa) is opened by a Cu(I)-salt-catalyzed Grignard reaction with a 4-bromobenzaldehyde ketal, preferably the 4-bromobenzaldehyde dimethyl ketal, to 11β-aryl-substituted 5α-hydroxy steroids of formula (IIIa)

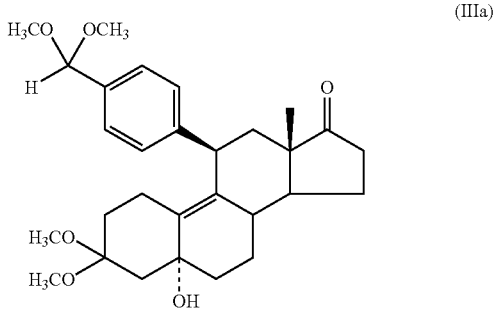

(IIIa)

In this case, the yields of the process are not optimal since a portion (3 to 10%) of the 17-oxo group is also attacked.

11β,17α-Bisaryl-substituted steroids of formula (IVa)

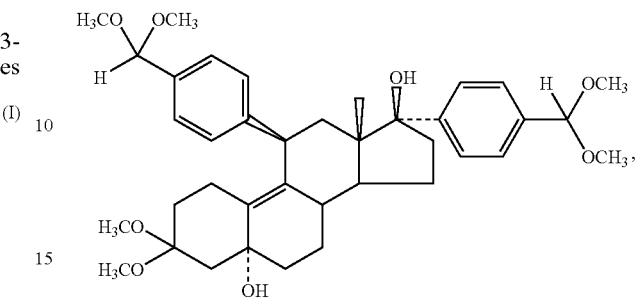

(IVa)

that are very difficult to separate by chromatography from the desired 11β-monoaryl-substituted compounds of formula (IIIa) are produced.

According to COREY and CHAYKOWSKY (J. Amer. Chem. Soc. 84, 3782 [1962]), the mixture of the compounds of formulas (IIIa) and (IVa) can be converted mainly into the spiroepoxide of formula (Va)

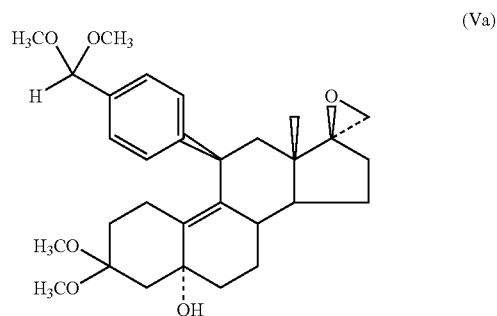

(Va)

which is opened by alkali methylate to a 17α-methoxy compound of formula (VIa)

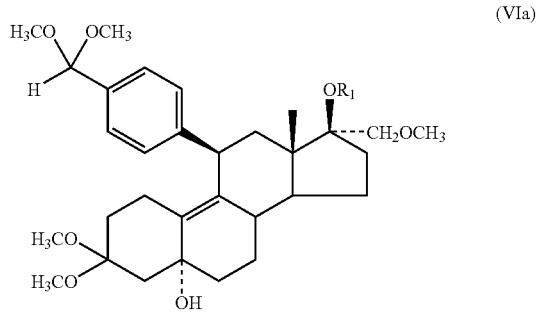

(VIa)

in which $R_1$ is a hydrogen atom and which is converted either immediately or after reaction of 17β-hydroxyl with alkyl halides in the presence of bases such as potassium-tert.-butanolate in inert solvents, such as tetrahydrofuran (THF) or toluene, into the 17β-ethers of formula (VIa), in which $R_1$ is a $C_{1-6}$-alkyl radical, by acid hydrolysis into the benzaldehydes of formula (VIIa)

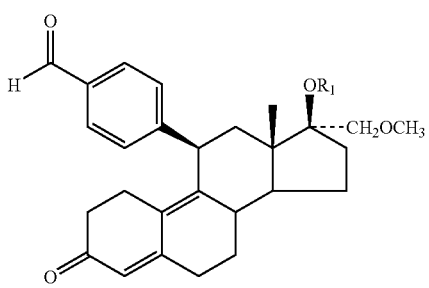

(VIIa)

in which $R_1$ is a hydrogen atom or a $C_{1-6}$-alkyl radical. The 11β,17β-bisaryl steroids of formula (IVa) that are produced in the Grignard reaction as by-products are constantly entrained under the above-mentioned conditions and ultimately hydrolyzed to the 11β,17α-bisaldehydes of formula (VIIIa)

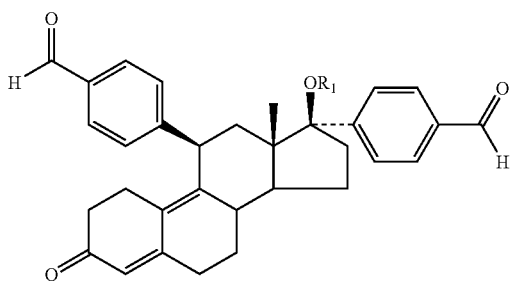

(VIIIa)

in which $R_1$ has the above-indicated meaning. These bisaldehydes of formula (VIIIa) differ in the crystallization behavior and in their chromatographic properties only very slightly from the monoaldehydes of formula (VIIa) and are difficult to separate largely quantitatively. These by-products pose a problem in the production of the compounds of formula (I) according to the invention.

The object of this invention is therefore to make available a more effective and technically simpler process for the production of 4-(17α-substituted-3-oxoestra-4,9-dien-11β-yl)benzaldehyde-(1E or 1Z)-oximes of general formula (I) that prevents the attack of the Grignard compound on the C-17 and thus produces the compounds of formula (I) with higher yield and purity.

This object is achieved according to the process of claim 1.

Since the 17-oxo group is converted into the desired 17α-substituted compound before the grignardization, the formation of the by-product of formula (VIIIa) is prevented, by which the target compounds are obtained with higher yield and purity. Thus, for example, using compound (II) as a starting material according to the process of DE 43 32 283 A1, aldehyde (VIIb) can be produced at a yield of about 5.6%, and accordingly oxime (Ic) can be produced at a yield of about 3.8%. By the process according to the invention, the aldehyde (VIIb) can now be produced at a yield of about 25% or the oxime (Ic) can be produced at a yield of about 17% from olefin (IX), without special chromatographic conditions having to be used for the purification.

Preferred embodiments of the invention are indicated in the subclaims. Because of additional advantages of the invention, reference is made to the following description and the embodiments.

According to the invention, the 3,3-dimethoxy-5α,10α-epoxy-estr-9(11)-en-17-ones of formula (II)

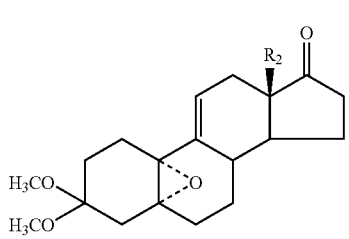

(II)

in which $R_2$ means a $C_{1-4}$-alkyl radical, are converted with an active methylene reagent, produced from, for example, trimethylsulfonium iodide, and a strong base, such as potassium-tert-butanolate or potassium hydroxide, in solvents, such as dimethyl sulfoxide (DMSO), dimethylformamide (DMF) or toluene, into the 5α,10α-epoxy-17(S)-spiroepoxide of formula (IX)

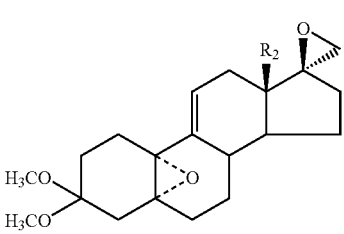

(IX)

whereby $R_2$ has the above-indicated meaning, which, after regio- and stereoselective cleavage of the 17-spiroepoxy group by alkali or alkaline-earth alcoholate, preferably by sodium methanolate, by alkylmercaptans in the presence of alkali hydroxides or potassium-tert-butanolate, alternatively directly with alkali mercaptides or with perfluoroalkyl alcohols in the presence of alkali, preferably potassium-tert-butanolate, in solvents, such as methanol, DMF or DMSO, is opened to to the 17α-substituted compounds of formula (X)

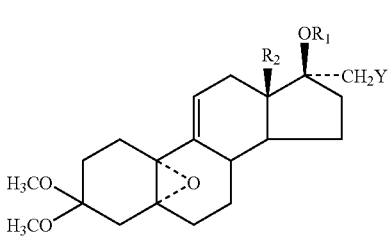

(X)

whereby Y means an $OC_{1-6}$-alkyl group, an $SC_{1-6}$-alkyl group or an $OCH_2C_nF_{2n+1}$ group, whereby n is 1, 2 or 3, and $R_1$ is a hydrogen atom, and $R_2$ has the above-mentioned meaning, which are converted as desired by reaction of the 17β-hydroxyl group with haloalkyl compounds or haloalkyl fluorides (halogen=Cl, Br or I) in the presence of strong bases such as potassium hydroxide, alcoholates, such as potassium-tert-butanolate, silver fluorides, alkali metals and naphthalene or biphenyl in inert solvents, such as ethers, THF or toluene, into the 17β-ethers or 17β-fluoroalkyl ethers of formula (X), in which $R_1$ is a $C_{1-6}$-alkyl radical or a $C_nF_{2n+1}$ radical, whereby n is 1, 2 or 3, and $R_2$ and Y have the above-mentioned meanings. The compounds of formula (X) are reacted with 4-bromobenzaldehyde ketals, such as the 4-bromobenzaldehyde-1,1-ethylene ketal or the 4-bromobenzaldehyde-1,1-dimethyl ketal, magnesium and Cu(I)Cl at temperatures of between −35° C. and room temperature to form the corresponding 3,3-dimethoxy-5α-hydroxy-11β-benzaldehyde ketals of formula (XI)

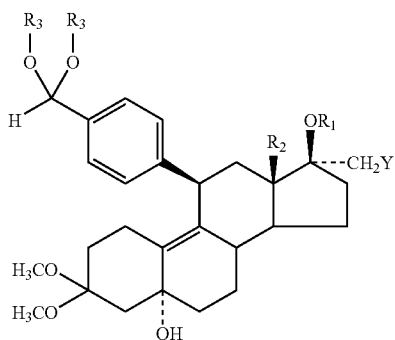

(XI)

in which $R_3$ stands for a methyl radical or an ethylidene group, and $R_1$, $R_2$ and Y have the above-indicated meanings, which are converted by acid hydrolysis of the protective groups, for example with dilute acetic acid or p-toluenesulfonic acid in acetone, into the 11β-benzaldehyde derivatives of formula (XII),

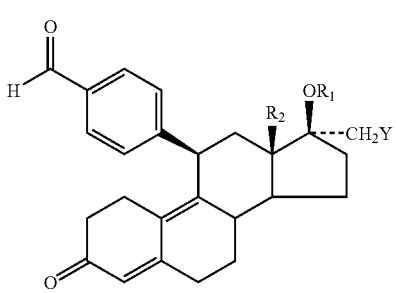

(XII)

in which $R_1$, $R_2$ and Y have the above-indicated meanings, and the aldehyde function is converted selectively by hydroxylammonium salts, preferably hydroxylamine hydrochloride in the presence of bases, preferably pyridine or triethylamine, at room temperature into a mixture of the E/Z-benzaldoximes of general formula (I)

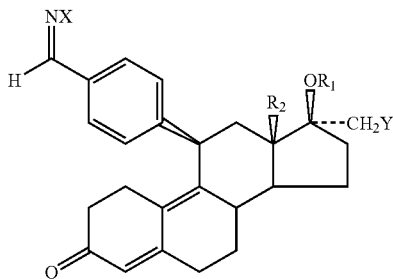

(I)

in which X means an OH group in E- or Z-position, and $R_1$, $R_2$ and Y have the above-indicated meanings, which are recrystallized or separated by chromatography, purified and isolated as individual components.

In this invention, "alkyl radical" is defined as a branched or straight-chain alkyl radical. As $C_{1-4}$- or $C_{1-6}$-alkyl radicals, for example, a methyl, ethyl, n-propyl, i-propyl, n-butyl, i-butyl or tert-butyl, n-pentyl, i-pentyl, n-hexyl, 2-methylpentyl, 3-methylpentyl, 2,2-dimethylbutyl or 2,3-dimethylbutyl group can be mentioned. A $C_nF_{2n+1}$ radical is defined as a branched or straight-chain fluoroalkyl radical with 1 to 3 carbon atoms, whereby examples are a trifluoromethyl, pentafluoroethyl, heptafluoro-n-propyl or heptafluoro-isopropyl group.

$R_1$ and $R_2$ preferably mean a $C_{1-3}$-alkyl radical, especially preferably a methyl group or a trifluoromethyl group.

Y preferably means an $OC_{1-3}$-alkyl radical or an $SC_{1-3}$-alkyl radical, especially preferably a methoxy, ethoxy, isopropyloxy, methylthio or ethylthio group, or a trifluoroethoxy group. The compounds of formula (I), in which $R_1$ is a $C_nF_{2n+1}$ radical and/or Y is an $OCH_2C_nF_{2n+1}$ group, are new.

Most preferred within the framework of the compounds of formula (I) are the following compounds:

4-[17β-Hydroxy-17α-(methoxymethyl)-3-oxoestra-4,9-dien-11β-yl]benzaldehyde-1E-oxime, 4-[17β-Hydroxy-17α-(methoxymethyl)-3-oxoestra-4,9-dien-11β-yl]benzaldehyde-1Z-oxime, 4-[17β-Methoxy-17α-(methoxymethyl)-3-oxoestra-4,9-dien-11β-yl]benzaldehyde-1E-oxime, 4-[17β-Methoxy-17α-(methoxymethyl)-3-oxoestra-4,9-dien-11β-yl]benzaldehyde-1Z-oxime, 4-[17β-Ethoxy-17α-(methoxymethyl)-3-oxoestra-4,9-dien-11β-yl]benzaldehyde-1E-oxime, 4-[17β-Hydroxy-17α-(ethoxymethyl)-3-oxoestra-4,9-dien-11β-yl]benzaldehyde-1E-oxime, 4-[17β-Methoxy-17α-(ethoxymethyl)-3-oxoestra-4,9-dien-11β-yl]benzaldehyde-1E-oxime, 4-[17β-Hydroxy-17α-(isopropyloxymethyl)-3-oxoestra-4,9-dien-11β-yl]benzaldehyde-1E-oxime, 4-[17β-Methoxy-17α-(isopropyloxymethyl)-3-oxoestra-4,9-dien-11β-yl]benzaldehyde-1E-oxime, 4-[17β-Hydroxy-17α-(ethylthiomethyl)-3-oxoestra-4,9-dien-11β-yl]benzaldehyde-1E-oxime and 4-[17β-Hydroxy-17α-(1,1,1-trifluoroethoxymethyl)-3-oxoestra-4,9-dien-11β-yl]benzaldehyde-1E-oxime.

The compounds are well bonded to the gestagen receptor, show a strong antigestagenic activity in the animal experiment, have a partial gestagenic activity and exhibit only slight gluocorticoid receptor binding (DE 4332283 A1 (EP 0 648 778 B1)).

The following examples are used for a more detailed description of the invention.

EXAMPLE 1

4-[17β-Hydroxy-17α-(methoxymethyl)-3-oxoestra-4,9-dien-11β-yl]benzaldehyde-1E-oxime (Ia)

Stage a 25 g of 3,3-dimethoxy-5α,10α-epoxy-estr-9(11)-en-17-one (IIa) is dissolved in 200 ml of DMSO and mixed with 34 g of trimethylsulfonium iodide. Then, 24 g of solid potassium-tert-butanolate is added, and it is stirred for 3 hours at room temperature, poured into ice-cold aqueous ammonium chloride solution, extracted with ethyl acetate, washed neutral, the organic phase is dried with sodium sulfate and concentrated by evaporation in a vacuum. 27 g of 3,3-dimethoxy-5α,10α-epoxy-estr-9(11)-ene-17(S)-spiroepoxide (IXa) is used as a sticky foam that is used directly in the next stage.

Stage b 27 g of 3,3-dimethoxy-5α,10α-epoxy-estr-9(11)-ene-17(S)-spiroepoxide (IXa) is dissolved in 100 ml of methanol, 100 ml of 3N sodium methylate solution is added under argon, and the mixture is refluxed for 2 hours. It is cooled, half of the methanol is distilled off, and the remainder is taken up in ethyl acetate, the solution is mixed with water, and the phases are separated. The organic phase is washed neutral, dried on sodium sulfate and concentrated by evaporation in a vacuum. 29.5 g of 3,3-dimethoxy-17α-(methoxymethyl)-5α,10α-epoxy-estr-9(11)-en-17β-ol (Xa) is obtained as a sticky foam, which is used directly in the next stage.

Stage c 10 g of 3,3-dimethoxy-17α-methoxymethyl-5α,10α-epoxy-estr-9(11)-en-17β-ol (Xa) in 50 ml of absolute THF is added in drops at −35° C. to a Grignard solution, produced from 2.7 g of magnesium, 25 g of 4-bromobenzaldehyde ethylene ketal in 130 ml of THF and 0.65 g of copper(I) chloride. It is allowed to heat to room temperature after 2 hours, decomposed with aqueous ammonium chloride solution, and the solution is extracted with tert-butyl methyl ether. The organic phase is washed neutral, dried and concentrated by evaporation in a vacuum. 16 g of a crude product is obtained, from which 4-(3,3-dimethoxy-5α,17β-dihydroxy-17α-methoxymethyl-estr-9-en-11β-yl)benzaldehyde-1,1-ethylene ketal (XIa) is isolated by chromatography on silica gel.

Melting point 111 to 116° C. $\alpha_D=-5°$ (CHCl$_3$). $^1$H-NMR: 7.36 (d, 2H, J=8.1, H3'), 7.24 (d, 2H, J=8.1, H2'), 5.76 (s, 1H, PhCH), 4.67 (s, 1H, OH), 4.27 (d, 1H, J=8.1, H-11α), 4.02–4.14 (m, 4H, ethylene ketal), 3.38 (s, 3H, OCH$_3$), 3.22 (s, 3H, OCH$_3$), 3.21 (s, 3H, OCH$_3$), 3.17 (d, 1H, J=9.0, CH$_2$O), 2.55 (s, 1H, OH), 0.46 (s, 3H, H-18).

Stage d 45 g of 4-(3,3-Dimethoxy-17α-methoxymethyl-5α-hydroxy-estr-9-en-11β-yl)benzaldehyde-1,1-ethylene ketal (XIa) is dissolved in 100 ml of tert.-butyl methyl ether, mixed with 1.2 g of p-toluenesulfonic acid and stirred for 1 hour at room temperature. After adding 15 ml of bicarbonate solution, it is extracted with methylene chloride, the organic phase is washed neutral, dried and concentrated by evaporation in a vacuum. After tert-butyl methyl ether is added, 4-[17β-hydroxy-(17α-(methoxymethyl)-3-oxoestra-4,9-dien-11β-yl]benzaldehyde (VIIa) precipitates as a crude product, which is purified by chromatography on silica gel and is recrystallized from ethyl acetate.

Melting point 235 to 240° C. $\alpha_D=+209°$ (CHCl$_3$). $^1$H-NMR: 9.97 (s, 1H, —CHO), 7.80 (d, 2H, J=8.1, H-3'), 7.38 (d, 2H, J=8.1, H-2'), 5.80 (s, 1H, H-4), 4.45 (d, 1H, J=7.5, H-11), 3.57 (d, 1H, J=9.2, CH$_2$O), 3.42 (d, 1H, J=10.8, CH$_2$O ), 3.41 (s, 3H, OCH$_3$), 0.51 (s, 3H, H-18).

Stage e 33 g of 4-[17β-hydroxy-17α-(methoxymethyl)-3-oxoestra-4,9-dien-11β-yl]benzaldehyde (VIIa) is dissolved under argon cover gas in 250 ml of pyridine and mixed with 5.8 g of hydroxylamine hydrochloride. After 2 hours, it is stirred in ice water, the precipitate is suctioned off, washed and dried. The crude product (40 g) is purified by chromatography on silica gel. 20 g of 4-[17β-hydroxy-(17α-(methoxymethyl)-3-oxoestra-4,9-dien-11β-yl]benzaldehyde-1E-oxime (Ia) [melting point 135 to 145° C. (EtOH/water), $\alpha_D=+236°$ (CHCl$_3$). $^1$H-NMR: 9.00 (s, 1H, NOH), 8.11 (s, 1H, HC=N), 7.45 (d, 2H, J=8.2, H-3'), 7.17 (d, 2H, J=8.2, H-2'), 5.79 (s, 1H, H-4), 4.38 (d, 1H, J=7.1, H-11), 3.58 (d, 1H, J=9.0, CH$_2$O), 3.43 (s, 3H, OCH$_2$), 3.25 (d, 1H, J=9.0, CH$_2$O), 0.48 (s, 3H, H-18)] and 1.5 g of 4-[17β-hydroxy-17α-(methoxymethyl)-3-oxoestra-4,9-dien-11β-yl]benzaldehyde-1Z-oxime (Ib) [melting point 135 to 146° C. (acetone), $\alpha_D=+192°$. $^1$H-NMR: 8.56 (s, 1H, NOH), 7.86 (d, 2H, J=8.4, H-3'), 7.33 (s, 1H, HC=N), 7.26 (d, 2H, J=8.4, H-2'), 5.79 (s, 1H, H-4), 4.41 (d, 1H, J=7.2, H-11), 3.57 (d, 1H, J=9.1, CH$_2$O), 3.42 (s, 3H, OCH$_3$), 3.23 (d, 1H, J=9.1, CH$_2$O), 0.54 (s, 3H, H-18).

EXAMPLE 2

4-[17β-Methoxy-17α-(methoxymethyl)-3-oxoestra-4,9-dien-11β-yl]benzaldehyde-1E-oxime (Ic)

Stage a 29.5 g of 3,3-dimethoxy-17α-methoxymethyl-5α,10α-epoxy-estr-9(11)-en-17β-ol (Xa) that is produced in Example 1, Stage b, is dissolved under argon in 650 ml of toluene, mixed with 110 g of potassium-tert-butanolate and stirred at room temperature. 70 ml of methyl iodide in 30 ml of toluene is added in drops within 2 hours. Then, it is diluted with water, the phases are separated, the organic phase is washed neutral, dried, and concentrated by evaporation in a vacuum. 30 g of 3,3,17β-trimethoxy-5α,10α-epoxy-estr-9(11)-ene-17α-methoxy-methyl ether (Xb) is obtained as a yellow resin that is treated with hexane.

Melting point 114 to 118° C. (hexane). $\alpha_D=+7°$ (CHCl$_3$). $^1$H-NMR: 6.00 (m, 1H, H-11), 3.57 (d, 1H, J=10.3, CH$_2$O), 3.36 (s, 3H, OCH$_3$), 3.30 (d, 1H, J=10.3, CH$_2$O), 3.28 (s, 3H, OCH$_3$), 3.19 (s, 3H, OCH$_3$), 3.13 (s, 3H, OCH$_3$), 0.88 (s, 1H, H-18).

Stage b 500 mg of copper(I) chloride is added at −35° to a Grignard solution, produced from 24 g of 4-bromobenzaldehyde ethylene ketal and 2.0 g of magnesium in 140 ml of THF. It is stirred for 20 minutes at this temperature, and a solution of 10 g of 3,3,17β-trimethoxy-5α,10α-epoxy-estr-9(11)-ene-17α-methoxymethyl ether (Xb) in 40 ml of THF is added in drops. Then, the reaction solution is allowed to heat to room temperature, the batch is decomposed with aqueous ammonium chloride solution, the solution is extracted with ethyl acetate, and the organic phase is washed with water; it is dried with sodium sulfate, and the solution is concentrated by evaporation in a vacuum. The crude product, 4-(3,3-dimethoxy-5α-hydroxy-17-methoxy-17α-methoxymethyl-estr-9-en-11β-yl)benzaldehyde-1,1-ethylene ketal (XIb), (15 g), is used directly in the next stage.

Stage c 15 g of the crude product 4-(3,3-dimethoxy-5α-hydroxy-17β-methoxy-17α-methoxymethyl-estr-9-en-11β-yl)benzaldehyde-1,1-ethylene ketal (XIb) is dissolved in 120 ml of acetone and mixed with 1.3 g of p-toluenesulfonic acid. After 1 hour, it is neutralized and diluted with water. In this case, 4-[17β-methoxy-17α-methoxymethyl]-3-oxoestra-4,9-dien-11β-yl]benzaldehyde (VIIb) precipitates, which is suctioned off and recrystallized in acetone.

Melting point 245 to 250° C. (acetone). $\alpha_D$=+193° (CHCl$_3$). $^1$H-NMR: 9.97 (s, 1H, CHO), 7.79 (d, 2H, J=8.1, H-3'), 7.37 (d, 2H, J=8.1, H-2'), 5.79 (s, 1H, H-4), 4.44 (d, 1H, J=7.5, H-11), 3.56 (d, 1H, J=10.8, CH$_2$O), 3.42 (d, 1H, J=10.8, —CH$_2$O), 3.41 (s, 3H, OCH$_3$), 3.25 (s, 3H, OCH$_3$), 0.51 (s, 3H, H-18).

Stage d 1.75 g of hydroxylamine hydrochloride is added to a solution of 10 g of 4-[17β-methoxy-17α-(methoxymethyl)-3-oxoestra-4,9-dien-11β-yl]benzaldehyde (VIIb) in 100 ml of pyridine at room temperature, and the mixture is stirred for 2 hours. It is poured into ice water, the precipitate is suctioned off, dried with calcium chloride, and the crude product is chromatographed on silica gel. 7 g of 4-[17β-methoxy-17α-(methoxymethyl)-3-oxoestra-4,9-dien-11β-yl]benzaldehyde-1E-oxime (Ic) [melting point 196 to 198° C. (EtOH/H$_2$O), $\alpha_D$=+220° (CHCl$_3$). $^1$H-NMR: 8.38 (s, 1H, NOH), 8.10 (s, 1H, HC=N), 7.47 (d, 2H, J=8.1, H-3'), 7.20 (d, 2H, J=8.1, H-2'), 5.79 (s, 1H, H-4), 4.38 (d, 1H, J=7.3, H-11), 3.58 (d, 1H, J=10.8, CH$_2$O), 3.41 (s, 3H, OCH$_3$), 3.41 (d, 1H, J=10.8, CH$_2$O), 3.25 (s, 3H, OCH$_3$), 0.54 (s, 3H, H-18)] and 300 mg of 4-[17β-methoxy-17α-(methoxymethyl)-3-oxoestra-4,9-dien-11β-yl]benzaldehyde-1Z-oxime (Id) [melting point 120 to 138° C. (acetone/n-hexane), $\alpha_D$=+217° (CHCl$_3$). $^1$H-NMR: 9.38 (s, 1H, NOH), 7.88 (d, 2H, J=8.9, H-3'), 7.33 (s, 1H, HC=N), 7.26 (d, 2H, J=8.9, H-2'), 5.79 (s, 1H, H-4), 4.39 (d, 1H, J=7.3, H-11), 3.58 (d, 1H, J=10.5, CH$_2$O), 3.42 (d, 1H, J=10.5, CH$_2$O), 3.41 (s, 3H, OCH$_3$), 3.26 (s, 3H, OCH$_3$), 0.54 (s, 3H, H-18) are obtained.

EXAMPLE 3

4-[17β-Ethoxy-17α-(methoxymethyl)-3-oxoestra-4,9-dien-11β-yl]benzaldehyde-1E-oxime (Ie)

Stage a 4.16 g of the 3,3-dimethoxy-17α-methoxymethyl-5α,10α-epoxy-estr-9(11)-en-17β-ol (Xa) that is produced in Example 1, Stage b, is reacted in portions with a total of 15.6 g of potassium-tert.-butanolate and 76 ml of iodoethane in 405 ml of toluene at 35° C. within 14 hours. For working-up, it is cooled to room temperature and water is added, whereby salts are dissolved. The phases are separated, and the aqueous phase is extracted again with toluene. The solution is washed, dried and concentrated by evaporation. 4.2 g of 3,3,-dimethoxy-5α,10α-epoxy-17β-ethoxy-estr-9(11)-ene-17α-methoxymethyl ether (Xc) is obtained as a crude product, which is used directly in the next stage.

Stage b 0.1 g of copper(I) chloride is added at −35° C. to a Grignard solution, produced from 5 g of 4-bromobenzaldehyde ethylene ketal and 0.45 g of magnesium in 60 ml of THF. It is stirred for 30 minutes at this temperature, and a solution of 2.5 g of 3,3-dimethoxy-5α,10α-epoxy-17β-ethoxy-estr-9(11)-ene-17α-methoxymethyl ether (Xc) in 15 ml THF is added in drops. Then, the reaction solution is allowed to heat to room temperature, the batch is decomposed with aqueous ammonium chloride solution, and 4-[3,3-dimethoxy-5α-hydroxy-17β-ethoxy-17α-(methoxymethyl)-estr-9-en-11β-yl]benzaldehyde-1,1-ethylene ketal (XIc) (4.5 g), which is used directly in the next stage, is isolated after the usual working-up.

Stage c 4.5 g of 4-[3,3-dimethoxy-5α-hydroxy-17β-ethoxy-17α-(methoxymethyl)-estr-9-en-11β-yl]benzaldehyde-1,1-ethylene ketal (Xc) is dissolved in 60 ml of acetone. 1.6 g of p-toluenesulfonic acid is added, and it is poured into ice water after 1 hour. The 4-[17β-ethoxy-17α-methoxymethyl)-3-oxoestra-4,9-dien-11β-yl]benzaldehyde (VIIc) that precipitates in this case is suctioned off, dried and recrystallized from acetone/hexane and again from tert-butyl methyl ether.

Melting point 164 to 167° C. $\alpha_D$=+199° (CHCl$_3$). $^1$H-NMR: 9.97 (s, 1H, CHO), 7.80 (d, 2H, J=8.1, H-3'), 7.37 (d, 2H, J=8.1, H-2'), 5.79 (s, 1H, H-4), 4.43 (d, 1H, J=7.5, H-11), 3.58 (d, 1H, J=10.8, CH$_2$O), 3.41 (m, 2H, CH$_2$O), 3.40 (s, 3H, OCH$_3$), 1.10 (t, 3H, Ethyl), 0.51 (s, 3H, H-18).

Stage d 1.7 g of 4-[17β-ethoxy(17α-methoxymethyl)-3-oxoestra-4,9-dien-11β-yl]benzaldehyde (VIIc) is stirred in 25 ml of pyridine with 250 mg of hydroxylamine hydrochloride for 1 hour at room temperature. Then, it is poured into 100 ml of ice water, the precipitate is suctioned off, washed neutral with water and dried with calcium chloride. The crude product (1.7 g) is purified by chromatography on silica gel. 890 mg of 4-[17β-ethoxy-17α-(methoxymethyl)-3-oxoestra-4,9-dien-11β-yl]benzaldehyde-1E-oxime (Ie) is obtained.

Melting point 184 to 187° C. (acetone/hexane). $\alpha_D$=+214° (CHCl$_3$). $^1$H-NMR: 9.10 (s, 1H, CH=N), 7.58 (s,1H, OH), 7.49 (d, 2H, J=8.4, H-3'), 7.21 (d, 2H, J=8.4, H-2'), 5.78 (s, 1H, H-4), 4.38 (d, 1H, J=6.9, H-11), 3.62 (d, 1H, J=10.8, CH$_2$O), 3.40 (s, 3H, OCH$_3$), 3.36 (d, 1H, J=10.8, CH$_2$O), 1.11 (t, 3H, CH$_2$CH$_3$), 0.54 (s, 3H, H-18).

EXAMPLE 4

4-[17β-Hydroxy-17α-(ethoxymethyl)-3-oxoestra-4,9-dien-11β-yl]benzaldehyde-1E-oxime (If)

The production is carried out according to Example 1, Stages 1b, 1c, 1d and 1e, whereby in Stage 1b, sodium ethylate is used instead of sodium methylate. Compound (1f) is isolated as a colorless foam.

$\alpha_D$=+226° (CHCl$_3$). 1H-NMR: 8.10 (s, 1H, HC=N), 7.71 (s, 1H, NOH), 7.47 (d, 2H, J=8.2, H-3'), 7.19 (d, 2H, J=8.2, H-2'), 5.78 (s, 1H, H-4), 4.38 (d, 1H, J=7.1, H-11), 3.58 (d, 1H, J=9.3, CH$_2$O), 3.55 (m, 2H, CH$_2$H$_5$), 3.25 (d, 1H, J=9.3, CH$_2$O), 2.17 (s, 1H, OH), 1.25 (t, 3H, CH$_2$H$_5$), 0.52 (s, 3H, H-18).

EXAMPLE 5

4-[17β-Methoxy-17α-(ethoxymethyl)-3-oxoestra-4,9-dien-11β-yl]benzaldehyde-1E-oxime (Ig)

The production of compound (Ig) is carried out according to Example 1, Stage b, whereby sodium ethylate is used instead of sodium methylate, and according to Example 2, Stages 2a, 2b, 2c and 2d.

Melting point 90 to 95° C. tert.-butyl methyl ether). $\alpha_D$=+177° (CHCl$_3$). $^1$H-NMR: 8.10 (s, 1H, HC=N), 7.60 (s, 1H, NOH), 7.47 (d, 2H, J=8.1, H-3'), 7.24 (d, 2H, J=8.1, H-2'), 5.79 (s, 1H, H-4), 4.37 (d, 1H, J=7.3, H-11), 3.63 (d, 1H, J=10.8, CH$_2$O), 3.55 (m, 2H, C$_2$H$_5$), 3.44 (d, 1H, J=10.8, CH$_2$O), 3.26, 3.22 (2s; and OCH$_3$ each), 1.27 (t, 3H, C$_2$H$_5$), 0.54 (s, 3H, H-18).

EXAMPLE 6

4-[17β-Hydroxy-17α-(isopropyloxymethyl)-3-ox-oestra-4,9-dien-11β-yl]benzaldehyde-1E-oxime (Ih)

The production of compound (Ih) is carried out according to Example 1, Stages 1b, 1c, 1d and 1e, whereby in Stage 1b, sodium isopropylate is used instead of sodium methylate.

Melting point 192 to 196° C. (decomposition; diethyl ether). $\alpha_D$=+186° (CHCl$_3$). $^1$H-NMR: 8.10 (s, 1H, HC=N), 8.08 (s, 1H, NOH), 7.48 (d, 2H, J=8.1, H-3'), 7.19 (d, 2H, J=8.1, H-2'), 5.79 (s, 1H, H-4), 4.38 (d, 1H, J=6.6, H-11), 3.6 (m, CH$_2$), 3.59 (d, 1H, J=9.3, CH$_2$O), 3.23 (d, 1H, J=9.3, CH$_2$O), 3.02 (s, 1H, OH), 1.21 (m, 6H, 2xCH$_3$), 0.52 (s, 3H, H-18).

EXAMPLE 7

4-[17β-Methoxy-17α-(isopropyloxymethyl)-3-ox-oestra-4,9-dien-11β- yl]benzaldehyde-1E-oxime (Ii)

The production of compound (Ii) is carried out according to Example 1, Stage b, with sodium ethylate instead of sodium methylate and according to Example 2, Stages 2a, 2b, 2c and 2d.

Melting point 143° C. (decomposition; acetone/hexane). $\alpha_D$=+199° (CHCl$_3$). $^1$H-NMR: 8.10 (s, 1H, HC=N), 8.0 (s, 1H, NOH), 7.48 (d, 2H, J=8.4, H-3'), 7.21 (d, 2H, J=8.1, H-2'), 5.79 (s, 1H, H-4), 4.37 (d, 1H, J=6.9, H-11), 3.62 (d, 1H, J=10.5, CH$_2$O), 3.59 (m, 2H, OCH(CH$_3$)$_2$), 3.43 (d, 1H, J=10.2, CH$_2$O),3.26 (s, 3H, OCH$_3$), 1.22 (t, 3H, C$_2$H$_5$), 0.54(s, 3H, H-18).

EXAMPLE 8

4-[17β-Hydroxy-17α-(ethylthiomethyl)-3-oxoestra-4,9-dien-11β-yl]benzaldehyde-1E-oxime (Ij)

The production of compound (Ij) is carried out according to Example 1, Stages 1b, 1c, 1d and 1e, whereby in Stage 1b, sodium thioethylate is used instead of sodium methylate.

Melting point 132 to 137° C. $\alpha_D$=+165° (CHCl$_3$). $^1$H-NMR: 8.10 (s, 1H, HC=N), 7.93 (s, 1H, NOH), 7.49 (d, 2H, J=8.4, H-3'), 7.19 (d, 2H, J=8.4, H-2'), 5.79 (s, 1H, H-4), 4.42 (d, 1H, J=7.2, H-11), 2.95 (d, 1H, J=13.2, CH$_2$S), 2.90 (s, 3H, OH), 2.71 (d, 1H, J=12.9, CH$_2$S), 2.6 (m, 2H, SCH$_2$—), 1.29 (t, 32H, SCH$_2$CH$_3$), 0.56 (s, 3H, H-18).

EXAMPLE 9

4-{17β-Hydroxy-17α-(1,1,1-trifluoroethoxymethyl)-3-oxoestra-4,9-dien-11β-yl]benzaldehyde-1E-oxime (Ik)

The production of compound (Ik) is carried out according to Example 1, Stages 1b, 1c, 1d and 1e, whereby in Stage 1b, 1,1,1-trifluoroethanol and potassium-tert-butanolate are used instead of sodium methylate.

Melting point 132 to 136° C. (diethyl ether). $\alpha_D$=+182° (CHCl$_3$). $^1$H-NMR: 8.10 (s, 1H, HC=N), 7.60 (s, 1H, NOH), 7.49 (d, 2H, J=8.4, H-3'), 7.20 (d, 2H, J=8.1, H-2'), 5.79 (s, 1H, H-4), 4.41 (d, 1H, J=7.2, H-11), 3.95 (m, 2H, OCH$_2$CF$_3$), 3.92 (d, 1H, J=8.7, CH$_2$O), 3.82 (d, 1H, J=9.0, CH$_2$O), 0.55 (s, 3H, H-18).

The invention claimed is:

1. A process for the production of 4-(17α-substituted-3-oxoestra-4,9-dien-11β-yl)benzaldehyde-(1E or 1Z)-oximes of formula (I),

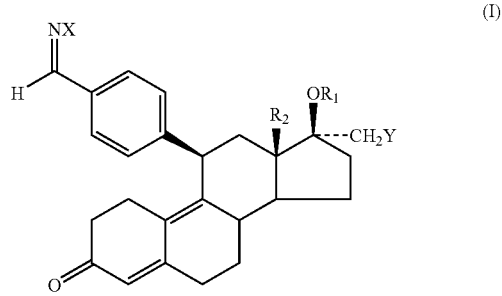
(I)

in which R$_1$ means a hydrogen atom, a C$_{1-6}$-alkyl radical or a C$_n$F$_{2n+1}$ radical, R$_2$ means a C$_{1-4}$-alkyl radical or trifluoromethyl, X means an OH group in E- or Z-position, and Y means an OC$_{1-6}$-alkyl group, an SC$_{1-6}$-alkyl group or an OCH$_2$C$_n$F$_{2n+1}$ group, whereby n is 1, 2 or 3, characterized in that a 3,3-dimethoxy-5α,10α-epoxy-estr-9(11)-en-17-one of formula (II)

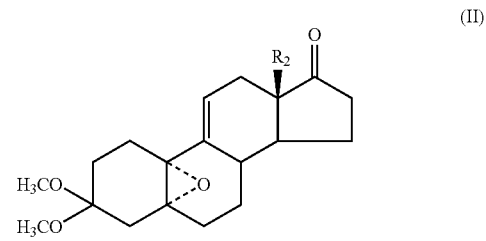
(II)

in which R$_2$ has the above-indicated meaning, is converted with an active methylene reagent in an inert solvent into a 5α,10α-epoxy-17(S)-spiroepoxide of formula (IX)

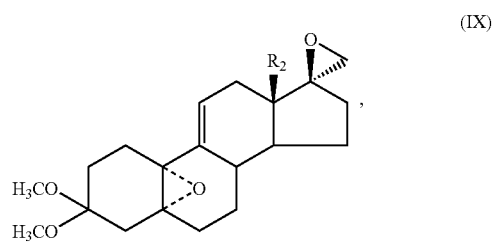
(IX)

in which R$_2$ has the above-indicated meaning, which, after regio- and stereoselective cleavage of the 17-spiroepoxy group by alkali or alkaline-earth alcoholate, by alkylmercaptans in the presence of alkali hydroxides or potassium-tert-butanolate, by direct cleavage with alkali mercaptides or with perfluoroalkyl alcohols in the presence of alkali in an inert solvent, is opened to a 17α-substituted compound of formula (X)

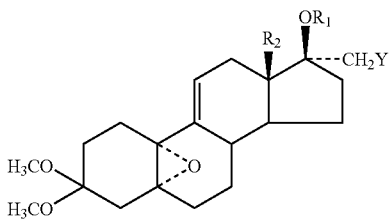

(X)

in which $R_1$ represents a hydrogen atom, Y means an $OC_{1-6}$-alkyl group, an $SC_{1-6}$-alkyl group or an $OCH_2C_nF_{2n+1}$ group, whereby n is 1, 2 or 3, and $R_2$ has the above-indicated meaning, which optionally is converted by reaction of the 17β-hydroxyl group with alkyl halides or haloalkyl fluorides in the presence of strong bases in an inert solvent into the 17β-ethers or 17β-fluoroalkyl ethers of formula (X), in which $R_1$ is a $C_{1-6}$-alkyl radical or a $C_nF_{2n+1}$ radical, whereby n is 1, 2 or 3, and $R_2$ and Y have the above-indicated meanings, which is reacted with a 4-bromobenzaldehyde ketal, magnesium and Cu(I)Cl at temperatures of between −35° C. and room temperature to form the corresponding 3,3-dimethoxy-5α-hydroxy-17α-$CH_2Y$-11β-benzaldehyde ketal of formula (XI)

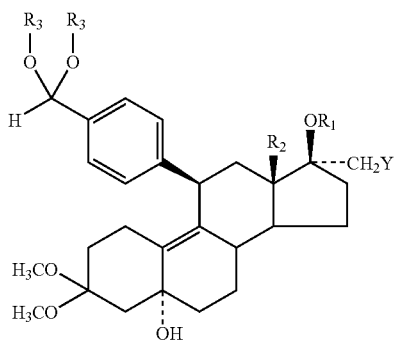

(XI)

in which $R_1$ is a hydrogen atom, a $C_{1-6}$ alkyl radical or a $C_nF_{2n+1}$ radical, whereby n is 1, 2 or 3, $R_2$ and Y have the above-indicated meanings, and $R_3$ stands for a methyl radical or an ethylidene group, which is converted by acid hydrolysis of the protective groups into an 11β-benzaldehyde derivative of formula (XII),

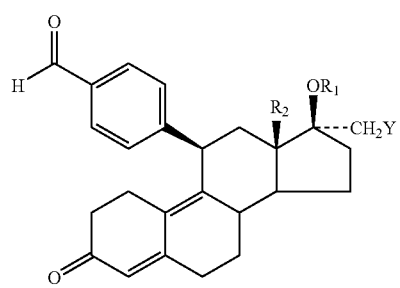

(XII)

in which $R_1$, $R_2$ and Y have the above-indicated meanings, and the aldehyde function is converted selectively by hydroxylammonium salts into a mixture of E/Z-benzaldoximes of formula (I),

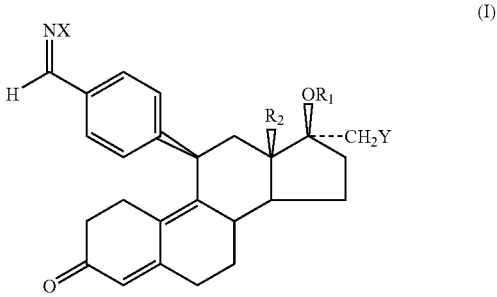

(I)

in which X means an OH group in E- or Z-position.

2. The process according to claim 1, additionally comprising separating the mixture of the E/Z-benzaldoximes of formula (I) by recrystallization or by chromatography into the individual components.

3. The process according to claim 1, wherein $R_1$ means a $C_{1-3}$-alkyl radical.

4. The process according to claim 1, wherein $R_2$ means a $C_{1-3}$-alkyl radical.

5. The process according to claim 1, wherein Y means an $OC_{1-3}$-alkyl radical or an $SC_{1-3}$-alkyl radical.

6. The process according to claim 3, wherein the compounds
4-[17β-Hydroxy-17α-(methoxymethyl)-3-oxoestra-4,9-dien-11β-yl]benzaldehyde-1E-oxime,
4-[17β-Hydroxy-17α-(methoxymethyl)-3-oxoestra-4,9-dien-11β-yl]benzaldehyde-1Z-oxime,
4-[17β-Methoxy-17α-(methoxymethyl)-3-oxoestra-4,9-dien-11β-yl]benzaldehyde-1E-oxime,
4-[17β-Methoxy-17α-(methoxymethyl)-3-oxoestra-4,9-dien- 11β-yl]benzaldehyde-1Z-oxime,
4-[17-Ethoxy-17α-(methoxymethyl)-3-oxoestra-4,9-dien-11β-yl]benzaldehyde-1E-oxime,
4-[17β-Hydroxy-17α-(ethoxymethyl)-3-oxoestra-4,9-dien-11β-yl]benzaldehyde-1E-oxime,
4-[17β-Methoxy-17α-(ethoxymethyl)-3-oxoestra-4,9-dien-11β-yl]benzaldehyde-1E-oxime,
4-[17β-Hydroxy-17α-(isopropyloxymethyl)-3-oxoestra-4,9-dien-11β-yl]benzaldehyde-1E-oxime,
4-[17β-Methoxy-17α-(isopropyloxymethyl)-3-oxoestra-4,9-dien-11β-yl]benzaldehyde-1E-oxime,
4-[17β-Hydroxy-17α-(ethylthiomethyl)-3-oxoestra-4,9-dien-11β-yl]benzaldehyde-1E-oxime or
4-{17β-Hydroxy-17α-(1,1,1-trifluoroethoxymethyl)-3-oxoestra-4,9-dien-11β-yl]benzaldehyde-1E-oxime are produced.

7. The process according to claim 3, wherein $R_1$ means a methyl or trifluromethyl group.

8. The process according to claim 4, wherein $R_2$ means a methyl or trifluromethyl group.

9. The process according to claim 5, wherein Y means a methoxy, ethoxy, isoproxy, methylthio, ethylthio or triofluroethoxymethyl group.

* * * * *

UNITED STATES PATENT AND TRADEMARK OFFICE
CERTIFICATE OF CORRECTION

PATENT NO.       : 7,214,808 B2                                        Page 1 of 1
APPLICATION NO.  : 10/416029
DATED            : May 8, 2007
INVENTOR(S)      : Gerd Schubert It is certified that error appears in the above-identified patent and that said Letters Patent is hereby corrected as shown below:

Column 14, formula (I) reads

" 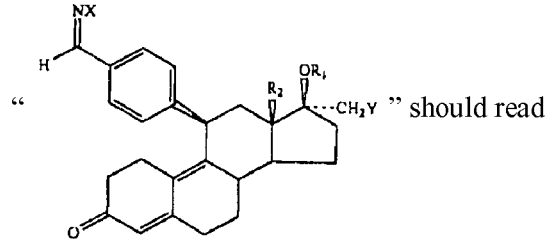 " should read

-- 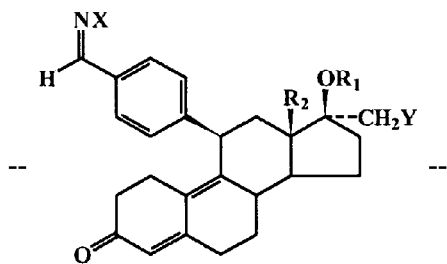 --

Column 14, line 41, reads "4-[17-Ethoxy" should read -- 4-[17β-Ethoxy --

Signed and Sealed this

First Day of July, 2008

JON W. DUDAS
*Director of the United States Patent and Trademark Office*